United States Patent [19]

Gray et al.

[11] 4,077,260
[45] Mar. 7, 1978

[54] OPTICALLY ACTIVE CYANO-BIPHENYL COMPOUNDS AND LIQUID CRYSTAL MATERIALS CONTAINING THEM

[75] Inventors: George William Gray, Cottingham; Damien Gerard McDonnell, Hull, both of England

[73] Assignee: The Secretary of State for Defence in Her Britannic Majesty's Government of the United Kingdom of Great Britain and Northern Ireland, London, England

[21] Appl. No.: 716,300

[22] Filed: Aug. 20, 1976

[30] Foreign Application Priority Data

Sep. 30, 1975 United Kingdom ............... 36211/75

[51] Int. Cl.² ......................... C09K 3/34; G02F 1/13; G01K 11/16
[52] U.S. Cl. ..................................... 73/356; 252/299; 260/465 C; 350/154; 350/350
[58] Field of Search ................. 252/299, 408; 350/154, 350/160 LC; 73/356; 260/465 C, 465 R

[56] References Cited

U.S. PATENT DOCUMENTS

| | | | |
|---|---|---|---|
| 3,597,044 | 8/1971 | Castellano | 252/299 |
| 3,642,348 | 2/1972 | Wysocki et al. | 252/299 |
| 3,680,950 | 8/1972 | Haas et al. | 252/299 |
| 3,704,056 | 11/1972 | Wysocki et al. | 252/299 |
| 3,833,287 | 9/1974 | Taylor et al. | 350/160 LC |
| 3,947,375 | 3/1976 | Gray et al. | 252/299 |
| 3,960,751 | 6/1976 | Moriyama et al. | 252/299 |
| 3,974,087 | 8/1976 | Gray et al. | 252/299 |
| 4,032,219 | 6/1977 | Constant et al. | 350/160 LC |
| 4,035,056 | 7/1977 | Coates et al. | 252/299 |

OTHER PUBLICATIONS

Gray, G. W. et al., Liquid crystals & Plastic Crystals, vol. 1, Ellis Horwood Ltd., London, pp. 142–143 (1974).

Gray, G. W. et al., Electronics Letters, vol. 9, No. 26, pp. 616–617 (Dec. 1973).

*Primary Examiner*—Richard E. Schafer
*Assistant Examiner*—T. S. Gron
*Attorney, Agent, or Firm*—Stevens, Davis, Miller & Mosher

[57] ABSTRACT

Liquid crystal compounds are disclosed having the formula

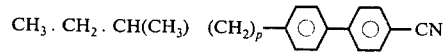

where $p$ is an integer having a value from 0 to 5 inclusive. These materials are optically active and cholesterogenic and may be used in an electro-optical display device either on their own or in admixture with nematogenic materials having a formula

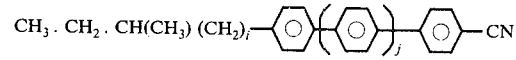

where $i$ has a value from 0 to 5 inclusive and $j$ is 0 or 1. These last mentioned mixtures may be thermochromic and employed in a temperature sensing device.

18 Claims, 4 Drawing Figures

OPTICALLY ACTIVE CYANO-BIPHENYL COMPOUNDS AND LIQUID CRYSTAL MATERIALS CONTAINING THEM

The present invention relates to optically active cyanobiphenyl compounds and liquid crystal materials and devices containing them.

U.K. patent specification No. 1,433,130 describes a family of compounds showing liquid crystal properties or tendencies, the family being characterised by the formula

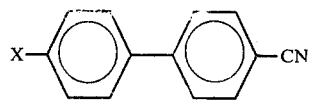

where CN is a cyano group and X is a terminal group, eg. an alkyl group. Members of this family show improved nematic liquid crystalline temperature ranges and also improved chemical and photochemical stability and are being used widely in liquid crystal devices.

According to the present invention in a first aspect a range of liquid crystal compounds which are specific members of the above family are characterised by the structural formula

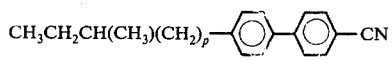

where $b$ is an integer having a value from 0 to 5 inclusive. These compounds will hereinafter be referred to as 'compounds of the range defined'.

These compounds are cholesterogenic and optically active. This means that the compounds exhibit either on their own or mixed with one or more liquid crystal compounds a cholesteric liquid crystal phase in which the molecules are arranged in a well known helical formation and that the molecules will rotate the plane of polarisation of polarised light.

According to the present invention in a second aspect a liquid crystal electro-optic display device incorporates in its liquid crystal material a compound of the range defined above either alone or in a mixture (solution) containing two or more compounds. The device may for example be a well known 'phase change' device in which the material is changed between a so called 'focal conic' cholesteric state which scatters light and a transparent nematic state by an applied electric field. The material may incorporate one or more pleochroic dyes such as described in copending United Kingdom Patent Application Nos. 25843/75 and 25859/75.

According to the present invention in a third aspect a liquid crystal material suitable for incorporating in the device in the second aspect defined above consists of a mixture of a compound of the range defined above with at least one nemotogenic compound having a formula

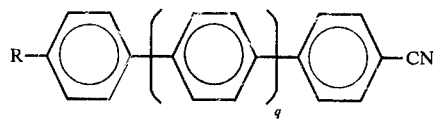

where $q$ is 0 or 1 and R is an n-alkyl or n-alkoxy group.

According to the present invention in a fourth aspect a material exhibiting a cholesteric liquid phase consists of a mixture of a compound of the range defined above with at least one compound having a structural formula

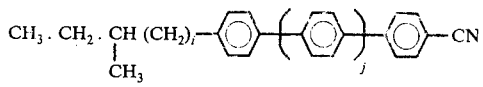

where $i$ is an integer having a value from 0 to 5 inclusive and $j$ is 0 or 1. This mixture may exhibit thermochromism. This means that the helical pitch length of its molecular formation is such as to give a strong temperature dependent Bragg reflection for a particular wavelength in the visible spectral region: in other words the material appears coloured with a colour which varies with the temperature of the material. The material may thus be used in surface thermography, e.g. for the detection of breast cancer.

According to the present invention in a fifth aspect a temperature sensitive colour display device includes one or more specimens of thermochromic liquid crystal material as defined in the fourth aspect above. Such a device gives a visual display resulting from the effect of temperature on the helical pitch of the material. The device may for example be a thermometer.

In the following description of this specification the following symbols are used (+): which refers to an optically active material having a positive optical rotation angle (−): which refers to an optically active material having a negative optical rotation angle $(\alpha)_D^{20}$ which is an absolute measure of the rotatory power (specific rotation) of an optically active material when forming a 10% w/v solution in chloroform.

Examples of the preparation of the compounds of the range defined above and of an optically active terphenyl compound suitable for mixing with them will now be described.

EXAMPLE 1

The preparation of (+)-4-(3″-methylpentyl)-4′-cyanobiphenyl by the following route

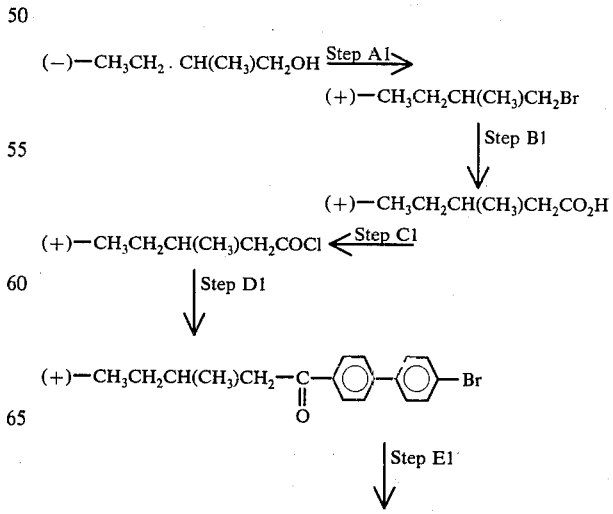

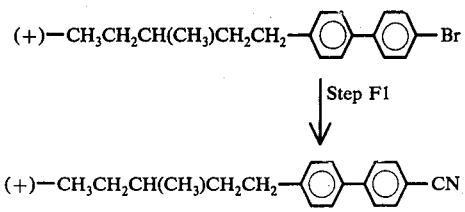

| Step F1

Step A1: The production of (+)-2-methylbutyl bromide

To a stirred solution of commercially available (−)-2-methylbutanol (0.34 mol) in dry 'Analar' (Trade Mark) pyridine (0.12 mol) is added in drops phosphorus tribromide (0.136 mol). The temperature during the addition is maintained below 15° C by cooking the mixture in an ice bath. The white emulsion which forms is stirred at room temperature for 2 hours. After this time the crude bromide is distilled from the emulsion under reduced pressure (300 mm Hg) until the mixture turns orange and 'seeths'.

The crude distillate is taken up in petroleum ether (b.p. 40°/60° C; 100 ml) and is washed with:
a. 5% sodium hydroxide solution (3 × 50 ml);
b. water (3 × 50 ml);
c. 10% sulphuric acid (2 × 50 ml);
d. concentrated sulphuric acid (100 ml);
e. water (2 × 100 ml).

The solution is dried over anhydrous sodium sulphate and the solvent is then evaporated off. The residue is distilled and the fraction boiling at 121° C collected (96.5% pure by g.l.c.). The product has $[\alpha]_D^{20}$ 3.9°.

Step B1: The production of (+)-3-methylpentanoic acid

Under anhydrous reaction conditions, the Grignard reagent from (+)-2-methylbutyl bromide (0.38 mol), produced by step A1, is prepared by conventional methods. The freshly made reagent is poured into crushed solid carbon dioxide (450g) in ether and the mixture is left stirring until a paste forms. The paste is acidified with 50% aqueous hydrochloric acid (240 ml). The combined ether layer and ether extracts of the aqueous layer are extracted with 25% sodium hydroxide solution (3 × 60 ml). The sodium hydroxide extracts are acidified with concentrated hydrochloric acid and then shaken with ether (4 × 100 ml). The ether extracts are washed with water (2 × 50 ml), dried over anhydrous sodium sulphate and the solvent is evaporated off. The residue is distilled under slight vacuum (450 mm Hg) and the fraction boiling at 136° C is collected $[\alpha]_D^{20}$ 6.4°.

Step C1: The production of (+)-3-methylpentanoyl chloride

The acid from step B1 is converted to its acid chloride using thionyl chloride according to a standard method. After removal of the excess of thionyl chloride, the residual acid chloride is used in step D1 without further purification.

Step D1: The production of (+)-4-(3″-methylpentanoyl)-4′-bromobiphenyl

To a mixture of anhydrous aluminium trichloride (0.1 mol) in dry dichloromethane (40 ml) is added in drops a mixture of 4-bromobiphenyl (0.086 mol) and (+)-3-methylpentanoyl chloride (0.1 mol) in dichloromethane (80 ml). The mixture is left stirring for 18 hours. After this time, the mixture is poured into a beaker containing, ice (100g), water (30 ml) and concentrated hydrochloric acid (50 ml) and left stirring for 0.5 hour. The organic layer is separated off, washed with water (2 × 40 ml), dried over anhydrous sodium sulphate and the solvent evaporated off. The crude product is then crystallised to constant melting point (97° C) from ethanol.

Step E1: The production of (+)-4-(3″-methylpentyl)-4′-bromobiphenyl

To lithium aluminum hydride (0.063 mol) in sodium dried ether (100 ml) are added:
a. anhydrous aluminum trichloride (0.135 mol) in sodium dried ether (100 ml) and
b. (+)-4-(3″-methylpentanoyl)-4′-bromobiphenyl (0.0185 mol) in dry chloroform (200 ml) at such a rate that the mixture gently boils.

The reaction mixture is then left stirring and boiling for 18 hours. The excess of lithium aluminium hydride is then destroyed by cautiously adding water to the mixture.

The mixture is then poured into a solution of ice (200 g), water (60 ml) and concentrated hydrochloric acid (100 ml) and left stirring for 0.5 hours.

The organic layer is separated off, washed with water (3 × 100 ml), dried over anhydrous sodium sulphate and the ether is then evaporated off. The solid product is recrystallised from ethanol to constant melting point (101°–102° C).

Step F1: The production of (+)-4-(-3″-methylpentyl)-4′-cyanobiphenyl

A mixture of (+)-4-(-3″-methylpentyl)-4′-bromobiphenyl (0.03 mol), which is the product from step E1, cuprous cyanide (0.03 mol) and N-methylpyrrolidone (38 ml) is heated under reflux and stirred for 2 hours. The cooled reaction mixture is poured into a solution of ferric chloride (12g) conc entrated hydrochloric acid (5 ml) and water (150 ml), and stirred at 60° C for 0.5 hour.

The organic material is then taken up in ether; the extract is washed with dilute hydrochloric acid (2 × 100 ml) and water (3 × 100 ml), dried over anhydrous sodium sulphate, and the solvent is then evaporated off.

The crude oily product is purified by column chromatography using a silica gel column and eluting with chloroform. The purified product is then distilled at 0.1 mm Hg, at an oil bath temperature of 180° C. Some constants measured for the product are given in Table 1 below.

EXAMPLE 2

The preparation of (+)-4-(4″-methylhexyl)-4′-cyanobiphenyl by the following route.

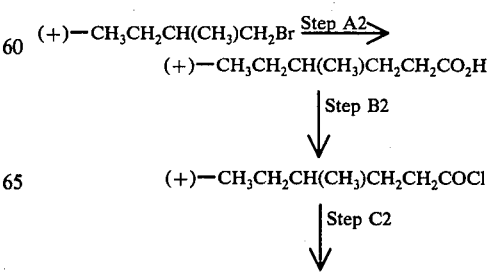

-continued

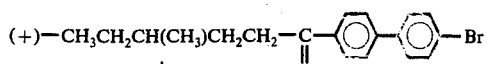

| Step D2

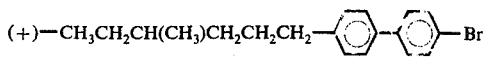

| Step E2

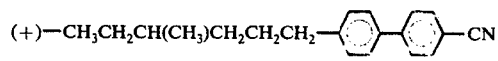

Step A2: The production of (+)-4-methylhexanoic acid (+)-2-Methylbutyl bromide, prepared as in step A1 of example 1, is converted into (+)-4-methylhexanoic acid by interaction with diethyl malonate followed by hydrolysis of the ester according to a literature method. The product (96% pure by g.l.c.) has an $[\alpha]_D^{20}$ 9.4° and boiled at 134° C at 25 mm Hg.

Step B2: The production of (+)-4-methylhexanoyl chloride

The acid from step A2 is converted into the acid chloride by interaction with thionyl chloride according to a standard method. After removal of the excess of thionyl chloride, the residual acid chloride is used in step C2 without further purification.

Step C2: The production of (+)-4-(4″-methylhexanoyl)-4′-bromobiphenyl

The acid chloride from step B2 in interacted with 4-bromobiphenyl by the method described in step D1 of example 1. The product is crystallised to constant melting point (56° C) from ethanol.

The product gives a monotropic smectric phase on cooling the isotropic liquid below the melting point to 28° C.

Step D2: The production of (+)-4-(4″-methylhexyl)-4-bromobiphenyl

This compound is prepared by a reduction method analogous to Step E1 of example 1. The solid product is crystallised to constant melting point (86°–89° C) from ethanol.

Step E2: The production of (+)-4-(4″methylhexyl)4′-cyanobiphenyl

This is prepared and purified by the a method analogous to step F1 of example 1. Some constants measured for the product are given in Table 1 below.

EXAMPLE 3

The preparation of (+)-4-(2″-methylbutyl)-4′-cyanobiphenyl by the following route:

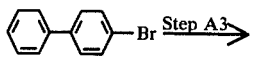

| Step B3

-continued

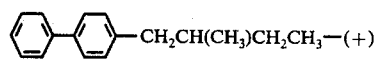

| Step C3

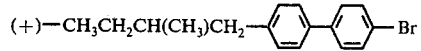

| Step D3

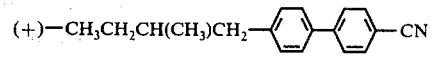

Step A3: The production of biphenylyl-4-magnesium bromide by the 'entrainment' method (+)-2-Methylbutyl bromide (0.07 mol), prepared as in Step A1 of example 1, in dry tetrahydrofuran (20 ml), is added to magnesium turnings (0.2 g atom) in dry tetrahydrofuran (20 ml) and the mixture is stirred for 0.5 hours. The reaction is initiated by a crystal of iodine and the rate of reaction is controlled by adding the alkyl bromide in drops.

4-Bromobiphenyl (0.13 mol) in dry tetrahydrofuran (20 ml) is then added in drops so as to maintain a steady refluxing of the solvent. When the addition is complete, the reaction mixture is stirred and heated under reflux for 4 hours and then left to stand overnight.

Step B3: The production of (+)-4-(2′-methylbutyl) biphenyl

The solution of the Grignard reagent, produced in Step A1, is cooled in an ice bath and, with vigorous stirring, a solution of ferric chloride (0.005 mol) in dry tetrahydrofuran (1.5 ml) is added in drops followed by a solution of (+)-2-methylbutyl bromide (0.2 mol) in dry tetrahydrofuran (20 ml). The mixture is stirred for 12 hours, then stirred and heated under reflux for 12 hours. After cooling, the mixture is poured into a beaker containing ice (200 g), water (400 ml) and concentrated hydrochloric acid (40 ml), and stirred for 0.5 hours.

The aqueous mixture is shaken with ether (4 × 200 ml) and the combined extracts are washed with water (3 × 100 ml) before drying over anhydrous sodium sulphate. The solvent is evaporated off and the crude oily product is purified using a silica gel column, eluting this with petroleum ether, b.p. 40°–60°. The purified product is then distilled at 0.1 mm Hg pressure.

Step C3: The production of (+)-4-(2″-methylbutyl)-4′-bromobiphenyl

Under anhydrous conditions, a solution of bromide (0.5 ml) in dry chloroform (5 ml) is added to (+)-4-(2′-methylbutyl) biphenyl (0.04 mol), produced in step B3, dissolved in dry chloroform (10 ml). The reaction mixture is kept at 0° C throughout the reaction time and light is excluded from the reaction vessel. After 18 hours and 36 hours two further additions (2 × 4 ml) of the chloroform solution of bromine (10% v/v) are added.

18 hours after the second addition, the mixture is poured into a sodium metabisulphite solution (150 ml). The aqueous solution is shaken with ether (3 × 80 ml). The combined extracts are washed with water (3 × 50 ml), dried over anhydrous sodium sulphate and the solvent evaporated off. The crude solid is recrystallised from ethanol to a constant melting point.

Step D3: The production of (+)-4-(2″-methylbutyl)-4′-cyanobiphenyl

This is prepared and purified by a method analogous to step F1 of example 1. Some constants for the product are given in Table 1 below.

EXAMPLE 4

The preparation of (+)-4-(3‴-methylpentyl)-4″ cyano-p-terphenyl by the following route:

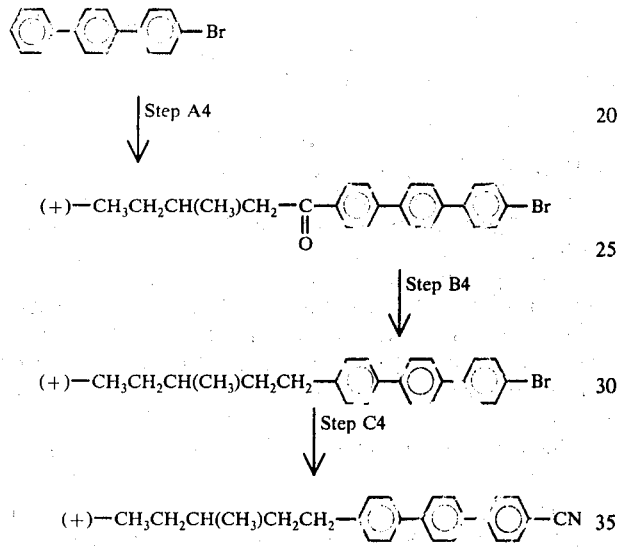

Step A4: The production of (+)-4-(3‴-methylpentanoyl)-4″-bromo-p-terphenyl (+)-3-Methylpentanoyl chloride prepared as in step C1 of example 1 is interacted with commercially available 4-bromo-p-terphenyl as in step D1 of example 1, but using more solvent.

The crude product is crystallised to constant melting point from 2-methoxyethanol; m.p. 196.1° C, giving a cholesteric phase until 197.8° C.

Step B4: The production of (+)-4-(3‴-methylpentyl)-4″-bromo-p-terphenyl

The ketone from step A3 is reduced in a manner analogous to step E1 of Example 1.

The crude product is crystallised to constant melting point (256° C) from toluene.

Step C4: The production of (+)-4-(3‴-methylpentyl)-4″-cyano-p-terphenyl (+)-4-(3‴-methylpentyl-4″-bromo-p-terphenyl is cyanated in a manner analogous to Step F1 of example 1, but using more solvent. The solid product is purified by column chromatography using a silica gel column and eluting with chloroform. The purified solid is sublimed at 0.05 mm Hg at an oil bath temperature of 180° C. Some constants measured for the products are given in Table 1 below.

TABLE 1

Physical constants for the compounds from examples 3, 1, 2 and abbreviated as 2M4CB, 3M5CB, 4M6CB and 3M5CT respectively.

| Compound | C-$S_A$ or I | $S_A$-Ch | Ch I | P | $[\alpha]_D^{20}$ | ΔH (kcal mol$^{-1}$) |
|---|---|---|---|---|---|---|
| 2M4CB | 4° C | (−54° C) | (−33° C) | 1.5 | 12.5 | 1.3 |
| 3M5CB | 9° C | (−22° C) | (−14) | 2.6 | 16.1° | 3.0 |
| 4M6CB | 28° C | (−20° C) | (−10) | 2.6 | 10.0° | 6.0 |
| 3M5CT | 144° C | (129° C) | 201° | 3.5 | 11.7° | 0.9 |

The key to the headings in Table 1 is as follows:
C-$S_A$ or I is the crystal to smectic or isotropic liquid transition temperature;
$S_A$-CH is the smectic to cholesteric liquid crystal transition temperature;
Ch-I is the cholesteric to isotropic liquid transition temperature;
P is the molecular helical pitch of the compound when forming 10% in a solution with 90% 4-n-pentyl-4′-cyanobiphenyl;
$[\alpha]_D^{20}$ is the rotatory power as defined above;
ΔH is the latent heat of melting.

The brackets around some of the transition temperature values indicate transitions which are not normally observed during melting but which may be observed by rapid cooling of the isotropic liquid.

Table 1 shows that although none of the compounds listed exhibits a cholesteric liquid phase at a temperature of general interest, e.g. room temperature, the compounds are potentially useful in mixtures with other liquid crytal compounds as materials which exhibit a cholestric phase at such temperatures.

The nematic analogues of the cholesteric compounds in Table 1 (for use in mixtures as described below) may be prepared by the methods described in Examples 1 – 4 by using racemic 2-methylbutanol as starting material.

The following are examples of mixtures which exhibit cholesteric phases at or near room temperature; the four compounds whose constants are listed in Table 1 are again referred to by the same abbreviations and the abbreviation 4M6CT refers to the following compound:

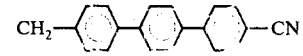

| Mixture 1 | Mixture 2 |
|---|---|
| 2M4CB | 2M4CB |
| 3M5CT | 4M6CT |

| Mixture 3 | Mixture 4 |
|---|---|
| 3M5CB | 3M5CB |
| 3M5CT | 4M6CT |

| Mixture 5 | Mixture 6 |
|---|---|
| 4M6CB | 4M6CB |
| 3M5CT | 4M6CT |

| Mixture 7 | Mixture 8 |
|---|---|
| 2M4CB | 2M4CB |
| Mixture 5 | Mixture 6 |

| Mixture 9 | Mixture 10 |
|---|---|
| 3M5CB | 4M6CB |
| Mixture 5 | Mixture 3 |

| Mixture 11 |
|---|
| 3M5CB |
| Mixture 8 |

Mixtures 1 to 11 all exhibit relatively short pitch cholesteric phases and thermochromism as defined above. The pitch lengths of the mixtures can also be adjusted by the addition of the nematic racemic analogues mentioned above. They are chemically more stable than the cholesteric materials, eg steryl esters, currently used in thermochromic devices and are hence potentially superior to the current materials in such devices.

Also, long pitch cholesteric mixtures may be provided by adding the compounds of the range defined above, or any Mixtures 1 to 11, to a cyanobiphenyl and/or cyanoterphenyl compound or mixture which is nematic at room temperature. Again, the resultant material is chemically more stable than the currently used cholesterol derivatives, e.g. cholesteryl nonanoate, and hence potentially superior in known 'phase change' electro-optic devices.

An example of a suitable phase change mixture is as follows:

Mixture 12

10% by weight of 3M5CB (as defined above) together with 90% by weight of nematic mixture M where M consists of:

| | |
|---|---|
| n-C$_5$H$_{11}$—◯—◯—CN | 43% by weight |
| n-C$_3$H$_7$O—◯—◯—CN | 17% by weight |
| n-C$_5$H$_{11}$O—◯—◯—CN | 13% by weight |
| n-C$_8$H$_{17}$O—◯—◯—CN | 17% by weight |
| n-C$_5$H$_{11}$—◯—◯—◯—CN | 10% by weight |

This mixture is preferably dyed, eg with a few percent by weight of the following pleochroic dye compound described in copending UK Patent Application No. 25859/75:

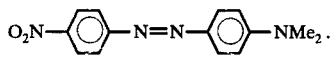

O$_2$N—◯—N=N—◯—NMe$_2$.

Any of the above mixtures may be provided in a known general way by adding the appropriate components together in a small beaker, raising the temperature above that at which the transistion to the clear isotropic liquid state occurs, maintaining the contents of the beaker above this transition temperature, whilst stirring, for about 20 minutes, and then slowly cooling the beaker.

Examples of devices embodying the invention will now be described by way of example with reference to the accompanying drawings, in which.

Figure 1:
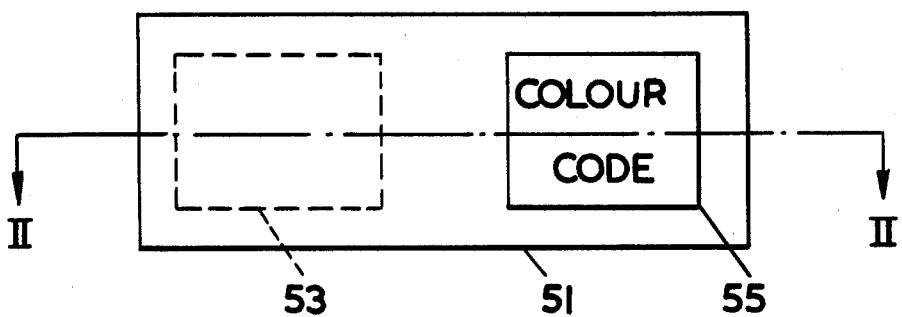
FIG. 1 is a front view of a temperature sensing device.
Figure 2:
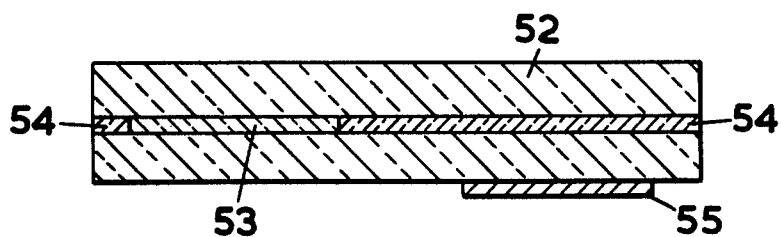
FIG. 2 is a cross-section of the line II—II of the device shown in FIG. 1.

In FIGS. 1 and 2 a region 53 of a chlolesteric liquid crystal mixture, eg one of Mixtures 1 to 9 defined above, in its so-called Grandjean plane texture is sandwiched between part of the inner surface area of two transparent slides 51, 52. The remainder of the space between th slides 51, 52 is filled with a filler 54, eg of Mylar (Trade Mark). A colour code label 55 is affixed to the front of the slide 51 in an area distinct from that of the liquid crystal region 53.

The device is used as follows. The region 53 is thermochromic, ie coloured with a colour dependent on temperature. Thus, as the temperature changes the colour of the region 53 changes. The label 55 provides a colour code by which an observer who sees a colour may note the corresponding temperature from the code. The code may be a table relating colour and temperature directly or a chart relating colour and, for example, a condition dependent on temperature, of a specimen being non-destructively tested.

Examples of specific mixtures for the region 53 and corresponding colour codes for the label 54 are as follows.

Mixture 13

14% by weight of (+)-4-(3'''-methylpentyl)-4''-cyano-p-terphenyl ($[\alpha]_D^{20} = 11.7°$)

and

86% by weight (+)-4-(3''-methylpentyl)-4'-cyanobiphenyl ($[\alpha]_D^{20} = 16.1°$)

| Colour Code for Mixture 13 | |
|---|---|
| Colour | Temperature ° C |
| Red | 5 |
| Yellow | 8 |
| Green | 9 |
| Turquoise | 12 |
| Blue | 14 |
| Isotropic liquid (clear) | 17.5 |

Mixture 14

14% by weight of (+)-4-(2''-methylbutyl)-4'-cyanobiphenyl ($[\alpha]_D^{20}$ 12.5°), 74% by weight of (+)-4-(4''-methylhexyl)-4'-cyanobiphenyl ($[\alpha]_D^{20}$ 10.0°) and 12% by weight of (+)-4-(4'''-methylhexyl)-4''-cyano-p-terphenyl ($[\alpha]_D^{20}$ 6.1°)

| Colour Code for Mixture 14 | |
|---|---|
| Colour | Temperature 0° C |
| Pink | −12 |
| Yellow | −11.5 |
| Green | −10.0 |
| Turquoise | − 8.5 |
| Blue | − 6.0 |
| Isotropic liquid (clear) | + 4 |

Several methods are known in the art for providing a sandwich structure as shown in FIGS. 1 and 2 with the cholesteric material in its Grandjean plane texture.

For example, one method is described in U.S. Pat. No. 3,440,882. A layer of the cholesteric material is spread on part of a sheet of acetate glass or Mylar (Trade Mark). A filler layer is then added and a further sheet of acetate glass or Mylar is used to complete the sandwich. The sandwich is then placed between two metal blocks of approximately the same surface area as the sheets. The blocks are then heated to a temperature of 40°–50° C whilst being pressed together to exert a force of about 5 lb on the sandwich. The metal blocks and the sandwich are then placed in a vacuum chamber and the pressure in the chamber is reduced to about 10 mm Hg for about a minute. After this time air is admitted providing a thin uniform liquid crystal layer in the sandwich.

Figure 3:
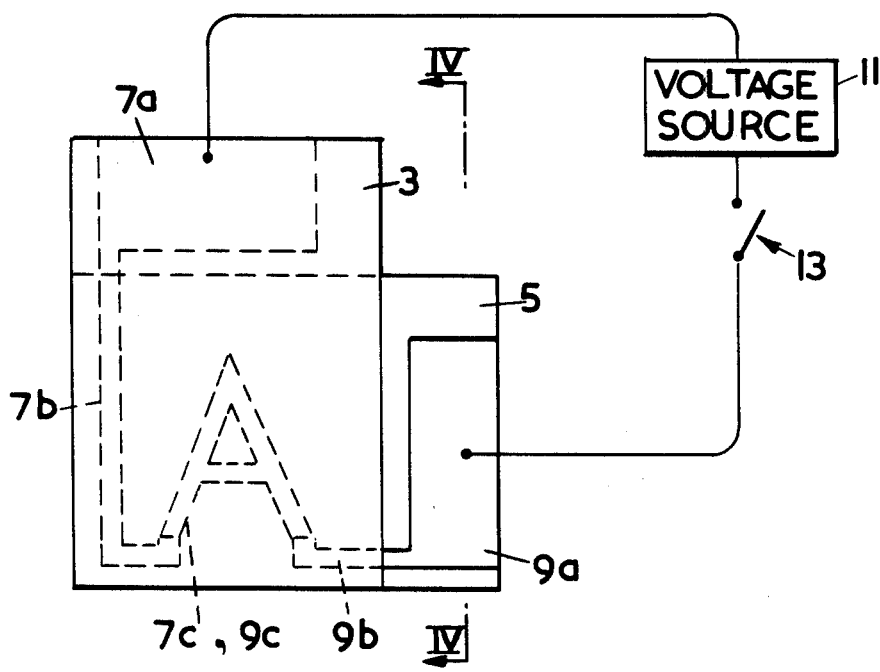
FIG. 3 is a front view, partly in circuit form, of a cholesteric-to-nematic phase change display device
Figure 4:
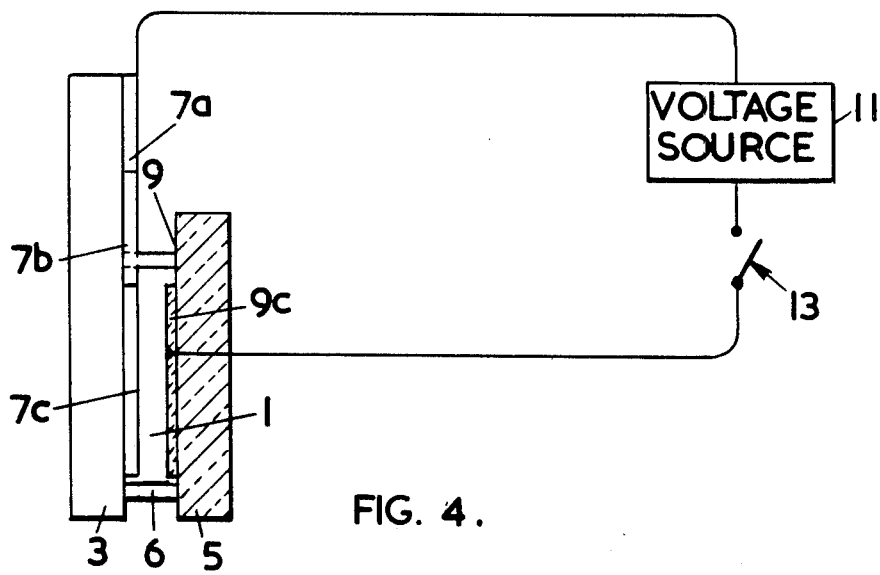
FIG. 4 is a cross-section, on the line IV—IV, of the device shown in FIG. 3.

As noted above the compounds of the range defined above may be used in mixtures to form phase-change effect materials. One example of the use of such mixtures is as follows:

FIGS. 3 and 4 show the construction of a phase change device incorporating a mixture such as Mixture 10 above. The device comprises a cell containing a dyed layer 1 of the liquid crystal mixture sandwiched between two parallel rectangular glass slides 3 and 5 having their respective longer edges perpendicular to one another and held apart by a ring-shaped spacer 6 (cut away for clarity in FIG. 2) defining the lateral extremities of the layer 1. The slides 3 and 5 both have on their respective inner surfaces electrodes 7 and 9. The electrode 7 is in the form of a patch 7a on an area of the slide 3 which does no face the slide 5, a strip 7b leading from the patch 7a and a portion 7c attached to the strip 7b and in the form of a letter A. The electrode 9 is in the form of a patch 9a on an area of the slide 5 which does not face the slide 3, a strip leading from the patch 9a and portion 9c attached to the strip 9b and which is in the form of the letter A. The portion 7c and the portion 9c are arranged to be identical and to face one another.

A voltage source 11 and a switch 13 in series with it are connected between the patch 7a and the patch 9a. The source 11 provides a voltage, which may be either direct ot alternating with a low frequency, sufficient to cause re-orientation of liquid crystal and dye molecules in the layer 1 to lie generally in the plane of the slides 3 and 5. A voltage of 10–20 volts will typically be required.

When the switch 13 is open the applied voltage is zero and the liquid crystal and dye molecules are arranged in an array of random helices (the 'focal conic' state) owing to the cholesteric nature of the liquid crystal material. The layer 1 thus appears strongly coloured with the colour of the dye, eg purple for the specific dye mentioned above, since white light incident on the layer 1 has a colour component absorbed by many of the dye molecules particularly those which are perpendicular or oblique to the propagation direction of the light.

When the switch 13 is closed the electric field produced by the voltage source 11 causes the cholestric to nematic phase change effect to occur. The liquid crystal molecules in the region between the portions 7c and 9c are re-oriented to lie perpendicular to the slides 3 and 5, ie parallel to the electric field, and the dye molecules in this region are re-orientated with the liquid crystal molecules. The layer 1 then appears clear or only weakly coloured between the portions 7c and 9c since the dye molecules do not significantly absorb light propagating along the direction of the electric field, ie along the long axis of the dye molecules. The remainder of the cell appears strongly coloured. If the electric field is removed the dye and liquid crystal molecules all return to their original helical arrangement.

Therefore the letter A may be displayed or not displayed by opening and closing the switch 13.

Preferably, the cell also includes a reflector (not shown) such as a white diffuse reflector, eg white card, a mirror, or a cardboard or plastic screen sprayed with aluminum paint, located behind the slide 5. If the device is then observed from in front of the slide 5 the reflector provides a more uniform background to the letter A.

Other letters, symbols or numerals or parts or groups of them may be displayed in a similar way.

I claim:

1. A liquid crystal material consisting essentially of an admixture of (1) one or more optically active biphenyl compounds having a positive optical rotation angle and having the formula:

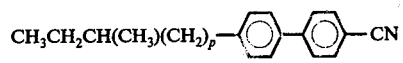

where $p$ is an integer having a value of from 0 to 5 inclusive and (2) at least one optically active cholesterogenic compound different from (1) having a positive optical rotation angle and having the formula:

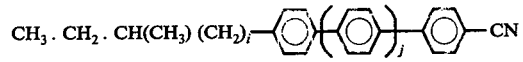

where $i$ is an integer having a value from 0 to 5 inclusive and $j$ is 0 or 1.

2. A liquid crystal material as claimed in claim 1 wherein said cholesterogenic compound is a terphenyl wherein $j$ is 1.

3. A liquid crystal material as claimed in claim 2 and wherein the cholesterogenic compound is
  (+)-4-(3'''-methylpentyl)-4''-cyano-p-terphenyl.

4. A liquid crystal material as claimed in claim 2 and wherein the cholesterogenic compound is
  (+)-4-(4'''-methylhexyl)-4''-cyano-p-terphenyl.

5. A liquid crystal material consisting essentially of a mixture of
  (+)-4-(2''-methylbutyl)-4'-cyanobiphenyl and (+)-4-(3'''-methypentyl)-4''-cyano-p-terphenyl.

6. A liquid crystal material consisting essentially of a mixture of
  (+)-4-(2''-methylbutyl)-4'-cyanobiphenyl and
  (+)-4-(4'''-methylhexyl)-4''-cyano-p-terphenyl.

7. A liquid crystal material consisting essentially of a mixture of
  (+)-4-(3''-methylpentyl)-4'-cyanobiphenyl and
  (+)-4-(3'''-methylpentyl)-4''-cyano-p-terphenyl.

8. A liquid crystal material consisting essentially of a mixture of
  (+)-4-(3''-methylpentyl)-4'-cyanobiphenyl and
  (+)-4-(4'''-methylhexyl)-4''-cyano-p-terphenyl.

9. A liquid crystal material consisting essentially of a mixture of
  (+)-4-(4''-methylhexyl)-4'-cyanobiphenyl and
  (+)-4(3'''methylpentyl)-4''-cyano-p-terphenyl.

10. A liquid crystal material consisting essentially of a mixture of
  (+)-4-(4''-methylhexyl)-4'-cyanobiphenyl and
  (+)-4(4'''-methylhexyl)-4''-cyano-p-terphenyl.

11. A liquid crystal material consisting essentially of a mixture of
  (+)-4-(2''-methylbutyl)-4''-cyanobiphenyl,
  (+)-4-(4''-methylhexyl)-4'-cyanobiphenyl and (+)-4-(3'''-methylpentyl)-4''-cyano-p-terphenyl.

12. A liquid crystal material consisting essentially of a mixture of
(+)-4-(2''-methylbutyl)-4'-cyanobiphenyl,
(+)-4-(4''-methyl hexyl)-4'-cyanobiphenyl and
(+)-4-(4'''-methyl hexyl)-4''-cyano-p-terphenyl.

13. A liquid crystal material consisting essentially of a mixture of
(+)-4-(3''-methylpentyl)-4'-cyanobiphenyl,
(+)-4(4''-methylhexyl)-4'-cyanobiphenyl and
(+)-4-(3'''-methylpentyl)-4''-cyano-p-terphenyl.

14. A liquid crystal material consisting essentially of a mixture of
(+)-4-(4''-methylhexyl)-4'-cyanobiphenyl,
(+)-4-(3''-methylpentyl)-4'-cyanobiphenyl and
(+)-4-(3'''-methylpentyl)-4''-cyano-p-terphenyl.

15. A liquid crystal material consisting essentially of a mixture of
(+)-4-(3''-methylpentyl)-4'-cyanobiphenyl,
(+)-4-(2''-methylbutyl)-4'-cyanobiphenyl,
(+)-4-(4''-methylhexyl)-4'-cyanobiphenyl and
(+)-4-(4'''-methylhexyl)-4''-cyano-p-terphenyl.

16. A temperature sensing device containing a cholesteric liquid crystal material consisting essentially of in admixture (1) one or more optically active biphenyl compounds having a positive optical rotation angle and having the formula:

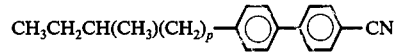

wherein $p$ is an integer having a value from 0 to 5 inclusive and (2) at least one optically active cholesterogenic compound different from (1) having a positive optical rotation angle and having the formula:

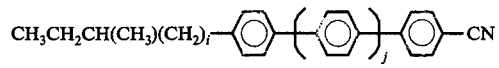

wherein $i$ is an integer having a value from 0 to 5 inclusive and $j$ is 0 or 1,
said liquid crystal material being sandwiched, in its Grandjean plane texture, between the inner surface area of two transparent slides.

17. A temperature sensing device as claimed in claim 16 and wherein the liquid crystal material consists of the following mixture
(+)-4-(3'''-methylpentyl)-4''-cyano-p-terphenyl — 14% by weight
(+)-4-(3''-methylpentyl)-4'-cyanobiphenyl — 86% by weight.

18. A temperature sensing device as claimed in claim 16 and wherein the liquid crystal material consists of the following mixture
(+)-4-(2''-methylbutyl)-4'-cyanobiphenyl — 14% by weight
(+)-4-(4''-methylexyl)-4'-cyanobiphenyl — 74% by weight
(+)-4-(4'''-methylhexyl)-4''-cyano-p-terphenyl — 12% by weight.

* * * * *